United States Patent [19]

Achard et al.

[11] Patent Number: 5,508,433
[45] Date of Patent: Apr. 16, 1996

[54] DERIVATIVES OF PERHYDROISOINDOLE AND PREPARATION THEREOF

[75] Inventors: Daniel Achard, Thiais; Serge Grisoni, Choisy-le-Roi, both of France; Stephen Hanessian, Beaconsfields, Canada; Claude Moutonnier, Le Plessis Robinson, France; Jean-Francois Peyronel, Palaiseau, France; Michel Tabart, Paris, France; Alain Truchon, Lyon, France

[73] Assignee: Rhone-Poulenc Rorer S.A., Antony, France

[21] Appl. No.: 146,142

[22] PCT Filed: May 15, 1992

[86] PCT No.: PCT/FR92/00430

§ 371 Date: Nov. 17, 1993

§ 102(e) Date: Nov. 17, 1993

[87] PCT Pub. No.: WO92/20654

PCT Pub. Date: Nov. 26, 1992

[30] Foreign Application Priority Data

May 17, 1991 [FR] France ................... 91 06036

[51] Int. Cl.[6] ........................................... C07D 209/48
[52] U.S. Cl. .............................................................. 548/515
[58] Field of Search ............................................. 548/515

[56] References Cited

U.S. PATENT DOCUMENTS 4,042,707  8/1977  Ripka ............................. 548/525
5,102,667  4/1992  Dubroeucq et al. ............ 514/416 X

FOREIGN PATENT DOCUMENTS

| 502760 | 8/1979 | Australia | C07D 209/44 |
| 058567 | 8/1982 | European Pat. Off. | C07C 103/52 |
| 068822 | 1/1983 | European Pat. Off. | C07D 207/44 |
| 093805 | 11/1983 | European Pat. Off. | C07D 209/44 |
| 359172 | 3/1990 | European Pat. Off. | C07D 209/52 |

*Primary Examiner*—Jacqueline Haley
*Attorney, Agent, or Firm*—Finnegan, Henderson, Farabow, Garrett & Dunner

[57] ABSTRACT

This invention relates to derivatives of perhydroisoindol of formula:

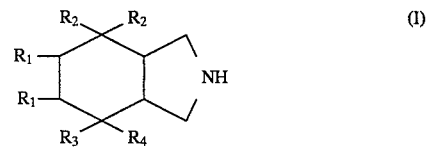

(I)

in which the radicals R are hydrogen atoms or together form a bond, the symbols $R_2$ are phenyl radicals which can be substituted by a halogen atom or a methyl radical in position 2 or 3, $R_3$ is a halogen atom or a hydroxy radical, $R_4$ is H or halogen if $R_3$ is halogen, in their isomer forms, or mixture thereof, and possibly also their salts when they exist, and preparation thereof. The derivatives of the invention are particularly interesting as P substance antagonist.

6 Claims, No Drawings

DERIVATIVES OF PERHYDROISOINDOLE AND PREPARATION THEREOF

This is a National Stage application of PCT/FR92/00430 filed May 15, 1992, published as WO/92/20654 on Nov. 26, 1992.

FIELD OF THE INVENTION

The present invention relates to new perhydroisoindole derivatives of general formula:

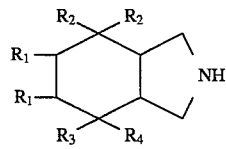

and their salts, which are intermediates in the preparation of perhydroisoindoles which antagonize the effects of substance P and are useful in the therapeutic sectors where this substance is known to play a role.

BACKGROUND OF THE INVENTION

Products derived from isoindole of general formula:

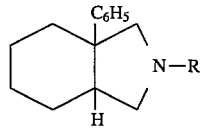

which exhibit opium activity, have been described in U.S. Pat. No. 4,042,707.

These products exhibit no activity towards substance P and neither can they be used as intermediates leading to such products.

In spite of the research carried out and in spite of the interest created [M. R. Hanley, TINS, (5) 139 (1982)], practically no product had been discovered so far which acts specifically on substance P and which has a nonpeptide structure; accordingly, the isoindole derivatives of general formula (I) are of great interest.

DESCRIPTION OF THE INVENTION

In the general formula (I):

the radicals $R_1$ are identical and represent hydrogen atoms or together form a bond, the symbols $R_2$ are identical and represent phenyl radicals which are optionally substituted by a halogen atom or by a methyl radical in position 2 or 3, the symbol $R_3$ represents a halogen atom or a hydroxyl radical and the symbol $R_4$ represents a hydrogen atom or, together with $R_3$, represents a halogen atom.

When $R_2$ carries a halogen substituent, or when $R_3$ is a halogen atom, the latter may be chosen from chlorine or fluorine.

Moreover, the products of general formula (I) having various stereoisomeric forms, it is understood that the isoindole derivatives of the (3aR, 7aR) form, in a pure state, or in the form of a mixture of the cis-(3aRS, 7aRS) forms, are included within the scope of the present invention. When the radicals $R_3$ and $R_4$ are different, it is also understood that the substituent $R_3$ may be in an axial or equatorial position and therefore that the R and S derivatives as well as mixtures thereof, are also included within the scope of the present invention.

According to the invention, the isoindole derivative of general formula (I) for which $R_3$ represents a halogen atom and $R_4$ represents a hydrogen or halogen atom, may be obtained by halogenation of the isoindole derivative of general formula:

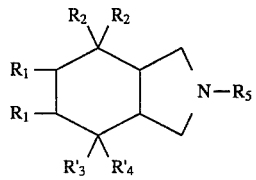

for which $R_1$ and $R_2$ are defined as above, $R'_3$ is a hydroxyl radical, $R'_4$ is a hydrogen atom if it is desired to obtain a monohalogenated derivative, or $R'_3$ and $R'_4$ together form an oxo radical if it is desired to obtain a dihalogenated derivative, followed by the removal of the protective radical $R_5$.

The protective radical $R_5$ may be any aminoprotecting group which is compatible with the reaction and whose introduction and removal does not affect the rest of the molecule. Alkoxycarbonyl groups, benzyloxycarbonyl groups, optionally substituted benzyl groups, formyl, chloroacetyl, trichloroacetyl, trifluoroacetyl, vinyloxycarbonyl, phenoxycarbonyl, 1-chloroethoxycarbonyl or chlorocarbonyl groups, may be mentioned by way of example.

When it is desired to obtain a product for which $R_3$ represents a fluorine atom, the reaction is advantageously carried out using a fluorinating agent such as sulphur fluoride (morpholinosulphur trifluoride, sulphur tetrafluoride (J. Org. Chem., 40, 3808 (1975)), diethylaminosulphur trifluoride (Tetrahedron, 44, 2875 (1988)), phenylsulphur trifluoride (J. Am. Chem. Soc., 84, 3058 (1962)], such as hexafluoropropyldiethylamine (Japanese Patent 2,039,546) or N-(2-chloro-1,1,2-trifluoroethyl)diethylamine, or selenium tetrafluoride (J. Am. Chem. Soc., 96, 925 (1974) or such as tetrafluorophenylphosphorane (Tet. Let., 907 (1973), by carrying out a procedure in an organic solvent such as a chlorine-containing solvent (for example dichloromethane, dichloroethane) at a temperature between −30 and +30° C. It is understood that the use of an alcohol of the (S) configuration leads to the fluorine-containing derivative of the (R) configuration and that the use of an alcohol of the (R) configuration leads to the fluorine-containing derivative of the (S) configuration. It is also possible to carry out the procedure using a mixture of alcohols of the (R) and (S) configurations and to carry out the separation with respect to the derivative of general formula (I) thus obtained.

When it is desired to obtain the difluorein-containing derivative of general formula (I), the reaction is carried out using the isoindolone of general formula (II) ($R'_3$ and $R'_4$ together form an oxo radical), carrying out the procedure under the conditions defined above, at a temperature between 30° C. and the reflux temperature of the reaction mixture.

When it is desired to obtain a product for which $R_3$ represents a chlorine atom, the chlorine-containing derivative of the (R) configuration may be obtained by treating the (S) alcohol with phosphorus pentachloride under the conditions defined by R. J. Cremlyn et al., J. Chem. Soc., 3794 (1954); the chlorine-containing derivative of the (S) configuration may be obtained by treating the (S) alcohol with thionyl chloride under the conditions stated by R. J. Cremlyn in the reference mentioned above.

When it is desired to obtain the dichlorine-containing derivative, the procedure is carried out using the perhydroisoindole of general formula (II), by treatment with phosphorus pentachloride under the conditions stated above.

The subsequent removal of the protective radical $R_5$ is carried out according to the usual methods. In particular, the procedure is carried out according to the methods described by T.W. Greene, Protective Groups in Organic Synthesis, A. Wiley—Interscience Publication (1981), or by Mc Omie, Protective Groups in Organic Chemistry, Plenum Press (1973).

According to the invention, the isoindole derivative of general formula (I) for which $R_3$ is a halogen atom and $R_4$ is a hydrogen atom, may also be obtained by halogenation of a perhydroisoindole derivative of general formula:

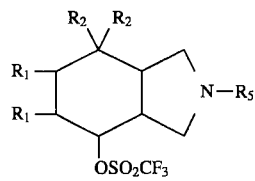

(III)

in which $R_1$, $R_2$ and $R_5$ are defined as above, followed by the removal of the protective radical $R_5$.

The halogenation is carried out using a quaternary ammonium halide such as for example tetrabutylammonium fluoride or using an alkali metal halide such as potassium fluoride or caesium fluoride for example, in an anhydrous medium, in an organic solvent such as an ether (for example tetrahydrofuran, dioxane), a chlorine-containing solvent (for example dichloromethane) or in a mixture of solvents, at a temperature between $-30°$ and $50°$ C.

It is understood that the sulphonylated derivative of general formula (III) of the (S) configuration leads to a halogenated derivative of the (R) configuration and that the sulphonylated derivative of the (R) configuration leads to a halogenated derivative of the (S) configuration.

The removal of the $R_5$ radical is carried out as described above.

The sulphonylated derivative of general formula (III) may be obtained by treating the perhydroisoindole derivative of general formula (II), for which $R'_3$ is a hydroxyl radical and $R'_4$ is a hydrogen atom, with a reactive trifluoromethanesulphonic acid derivative.

The reaction is generally carried out by reaction of the trifluoromethanesulphonic anhydride in the presence of pyridine, in a chlorine-containing solvent (for example dichloromethane), at a temperature between $-30°$ and $20°$ C.

According to the invention, the perhydroisoindole derivative of general formula (I), for which $R_3$ is a hydroxyl radical and $R_4$ is a hydrogen atom, may be obtained by reduction of the perhydroisoindolone derivative of general formula:

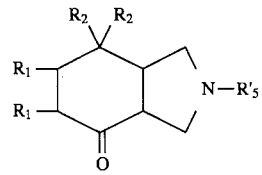

(IV)

in which $R_1$ and $R_2$ are defined as above and $R'_5$ is defined as $R_5$ or represents a hydrogen atom, followed by the separation of the axial and equatorial isomers and/or followed by the removal of the protective radical when $R'_5$ is other than a hydrogen atom.

The reduction is advantageously carried out using an alkali metal borohydride (sodium borohydride, lithium tri-s-butylborohydride), in a solvent such as an alcohol (for example methanol, ethanol) or an ether (tetrahydrofuran) in a basic medium or using an aluminohydride (for example aluminium and lithium hydride), at a temperature between $-20°$ and $50°$ C.

The removal of the radical $R'_5$ is carried out according to known methods which do not affect the rest of the molecule.

According to the invention, the hydroxylated perhydroisoindole derivative of general formula (I), in which $R_3$ is a hydroxyl radical and $R_4$ is a hydrogen atom, may also be obtained by releasing the protective radical $R_5$ from the corresponding perhydroisoindole derivative of general formula (II) in which $R'_3$ and $R'_4$ are defined as above.

The removal is carried out according to known methods which do not affect the rest of the molecule, in particular according to the methods stated above.

The perhydroisoindole derivative of general formula (II), or the perhydroisoindole derivative of general formula (IV) for which $R'_5$ is defined as $R_5$, may be prepared by protecting the amino of the corresponding derivative of general formula:

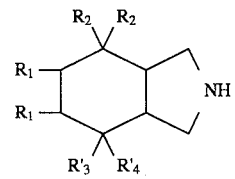

(V)

in which $R_1$, $R_2$, $R'_3$ and $R'_4$ are defined as for the general formula (II).

The protection is carried out according to the usual methods, in particular according to the references mentioned above.

The isoindole derivative of general formula (IV) for which $R'_5$ is a hydrogen atom, or (V) for which $R'_3$ and $R'_4$ together form an oxo radical, may be obtained from the corresponding derivative of general formula:

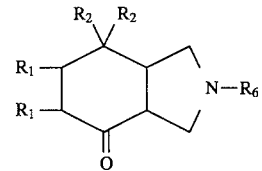

(VI)

in which $R_1$ and $R_2$ are defined as above and $R_6$ represents an allyl radical or a radical of the structure $-CR_aR_bR_c$ in which $R_a$ and $R_b$ are hydrogen atoms or phenyl radicals which are optionally substituted (by a halogen atom, an alkyl, alkoxy or nitro radical), and $R_c$ is defined as $R_a$ and $R_b$ or represents an alkyl or alkoxyalkyl radical, at least one of $R_a$, $R_b$ and $R_c$ being a substituted or unsubstituted phenyl radical and the alkyl radicals containing 1 to 4 carbon atoms in a linear or branched chain, by removing the radical $R_6$ by any known method which does not affect the rest of the molecule.

In particular, when $R_1$ is a hydrogen atom, and when $R_6$ is other than an allyl radical, the group $R_6$ may be removed by catalytic hydrogenation in the presence of palladium. Generally, the reaction is carried out in an acidic medium, in a solvent such as an alcohol (methanol, ethanol), in water or directly in acetic acid or formic acid, at a temperature between $20°$ and $60°$ C.

When $R_6$ is a benzohydryl or trityl radical, the removal may be carried out by treatment in an acidic medium, by carrying out the procedure at a temperature of between $0°$ C. and the reflux temperature of the reaction mixture, in an alcohol, in an ether, in water or directly in acetic acid, formic acid or trifluoroacetic acid. The group $R_6$ may also be removed by reaction of vinyl chloroformate, 1-chloroethyl chloroformate or phenyl chloroformate, a product of general formula:

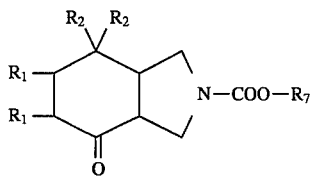

in which $R_1$ and $R_2$ are defined as above, and $R_7$ is a vinyl, 1-chloroethyl or phenyl radical, being obtained as an intermediate, and then by removing the radical —COOR$_7$ by acid treatment. The reaction of the chloroformate is generally carried out in an organic solvent such as a chlorine-containing solvent (for example dichloromethane, dichloroethane, chloroform), an ether (for example tetrahydrofuran, dioxane) or a ketone (for example acetone) or in a mixture of these solvents, by carrying out the procedure at a temperature between 20° C. and the reflux temperature of the reaction mixture.

The removal of the radical —COOR$_7$ is carried out by treatment in an acidic medium for example with trifluoroacetic, formic, methanesulphonic, p-toluenesulphonic, hydrochloric or hydrobromic acid in a solvent such as an alcohol, an ether, an ester, a nitrile, a mixture of these solvents or in water, at a temperature between 0° C. and the reflux temperature of the reaction mixture.

Under the conditions for removing the radicals —COOR$_7$ mentioned above, the expected isoindolone derivative of general formula (IV) or (V) is obtained in the form of a salt of the acid used, which may be used directly in the subsequent stage.

The isoindolone derivative of general formula (VI) may be obtained by cycloaddition reaction, by reaction of a silylated derivative of general formula:

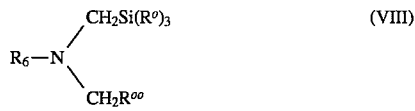

in which $R_6$ is defined is defined as above, $(R°)_3$ represents alkyl radicals or alkyl and phenyl radicals and $R°°$ represents an alkoxy, cyano or phenylthio radical, with the cyclohexenone derivative of general formula:

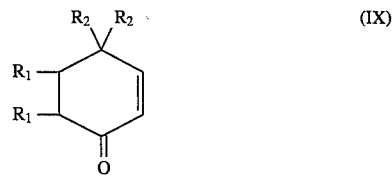

in which $R_1$ and $R_2$ are defined as above.

The procedure is carried out in the presence of a catalytic amount of an acid chosen from trifluoroacetic acid, acetic acid, methanesulphonic acid or the acids given in the references mentioned below, in an organic solvent such as a chlorine-containing solvent (for example dichloromethane, dichloroethane), in an aromatic hydrocarbon, in a nitrile (acetonitrile) or in an ether, at a temperature of between 0° C. and the reflux temperature of the reaction mixture.

The silylated derivative of general formula (VIII) may be obtained according to the methods described by:

Y. Terao et al., Chem. Pharm. Bull., 33, 2762 (1985);

A. Hosomi et al., Chem. Lett., 1117 (1984)

A. Padwa et al., Chem. Ber., 119, 813 (1986) or

Tetrahedron, 41, 3529 (1985).

It is understood that the perhydroisoindole derivatives of general formula (I), (II), (III), (IV), (V), (VI) and (VII) have several stereoisomeric forms. When it is desired to obtain a product of general formula (I) of the (3aR, 7aR) form, the separation of the isomeric forms may be carried out with respect to the derivative of general formula (V) for which R'$_3$ and R'$_4$ together form an oxo radical. It may also be carried out with respect to the derivative of general formula (I). The separation is carried out according to any known method which is compatible with the molecule.

By way of example, the separation may be carried out by the preparation of an optically active salt, by reaction of L(+) or D(−)-mandelic acid, or of dibenzoyltartaric acid, followed by separation of the isomers by crystallization. The desired isomer is released from its salt in a basic medium.

The separation of the axial and equatorial isomers of the hydroxylated derivatives or of the halogenated derivatives is advantageously carried out with respect to the products of general formula (II) or (V), the procedure being carried out using crystallization and/or chromatography. It is also possible to carry out the procedure with respect to the products of general formula (I).

According to the invention, the isoindole derivatives of general formula (I) may be used for the preparation of derivatives of general formula:

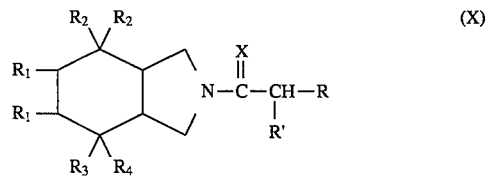

in which the symbol X represents an oxygen atom or an NH radical, the symbol R represents a phenyl radical which is optionally substituted by one or more halogen atoms or hydroxyl or alkyl radicals which may be optionally substituted (by halogen atoms or amino, alkylamino or dialkylamino radicals) alkoxy or alkylthio radicals which may be optionally substituted [by hydroxyl, amino, alkylamino or dialkylamino radicals optionally substituted (by phenyl, hydroxyl or amino radicals) or by dialkylamino radicals whose alkyl parts form with the nitrogen atom to which they are attached, a heterocycle with 5 to 6 members which may contain another heteroatom chosen from oxygen, sulphur or nitrogen, optionally substituted by an alkyl, hydroxyl or hydroxyalkyl radical)], or which is substituted by amino, alkylamino or dialkylamino radicals whose alkyl parts may form with the nitrogen atom to which they are attached, a heterocycle as defined above, or represents a cyclohexadienyl, naphthyl or a saturated or unsaturated, mono- or polycyclic heterocyclic radical containing 5 to 9 carbon atoms and one or more heteroatoms chosen from oxygen, nitrogen or sulphur, the symbol R' represents a hydrogen or halogen atom or a hydroxyl, alkyl, aminoalkyl, alkylaminoalkyl, dialkylaminoalkyl, alkoxy, alkylthio, acyloxy, carboxyl, alkoxycarbonyl, dialkylaminoalkoxycarbonyl, benzyloxycarbonyl, amino, acylamino or alkoxycarbonylamino radical, and the symbols $R_1$, $R_2$, $R_3$ and $R_4$ are defined as for the general formula (I);

the abovementioned alkyl or acyl radicals containing 1 to 4 carbon atoms in a linear or branched chain; when R contains a halogen atom, the latter being chosen from chlorine, bromine, fluorine or iodine;

when R represents a saturated or unsaturated, mono- or polycyclic heterocyclic radical, it being possible for the latter to be chosen from thienyl, furyl, pyridyl, dithiinyl, indolyl, isoindolyl, thiazolyl, isothiazolyl, oxazolyl, imidazolyl, pyrrolyl, triazolyl, thiadiazolyl, quinolyl, isoquinolyl, naphthyridinyl;

when R represents a phenyl which is substituted by a chain carrying a heterocycle, it being possible for the latter to be chosen from pyrrolidinyl, morpholino, piperidinyl, tetrahydropyridinyl, piperazinyl or thiomorpholino.

Furthermore, when the symbol R' is other than a hydrogen atom, the substituted chain on the isoindole has a chiral center, it is understood that the stereoisomeric forms and mixtures thereof are also included in the general formula (X).

According to the invention, the perhydroisoindole derivatives of general formula (I) may be obtained by reaction of the acid of general formula:

$$R-\underset{\underset{R'}{|}}{CH}-COOH \qquad (XI)$$

or of a reactive derivative of this acid, in which R and R' are defined as above, with an isoindole derivative of general formula (I) in which the symbols $R_1$, $R_2$, $R_5$ and $R_4$ are defined as above, followed, where appropriate, by conversion of the amide obtained to an amidine.

It is understood that the amino, alkylamino or carboxyl radicals contained in R and/or R' are preferably protected beforehand. The protection is carried out using any compatible group whose introduction and removal do not affect the rest of the molecule. In particular, the protection is carried out according to the methods described by T. W. Greene, by A. Wiley or by Mc Omie in the references mentioned above.

By way of example, the amino or alkylamino groups may be protected with the following radicals: methoxycarbonyl, ethoxycarbonyl, t-butoxycarbonyl, allyloxycarbonyl, vinyloxycarbonyl, trichloroethoxycarbonyl, trichloroacetyl, trifluoroacetyl, chloroacetyl, trityl, benzhydryl, benzyl, allyl, formyl, acetyl, benzyloxycarbonyl or its substituted derivatives;

the acidic groups may be protected with the following radicals: methyl, ethyl, t-butyl, benzyl, substituted benzyl or benzhydryl.

Furthermore, when R' represents a hydroxyl radical, it is preferable to protect this radical beforehand. The protection is carried out for example using an acetoxy, trialkylsilyl or benzyl radical or in the form of a carbonate using a —COORa radical in which Ra is an alkyl or benzyl radical.

When the condensation of a reactive derivative of the acid of general formula (XI) is carried out, the procedure is advantageously carried out using the acid chloride, the anhydride, a mixed anhydride or a reactive ester in which the ester residue is a succinimido radical, an optionally substituted 1-benzotriazolyl radical, a 4-nitrophenyl, 2,4-dinitrophenyl, pentachlorophenyl or phthalimido radical.

The reaction is generally carried out at a temperature of between −40° and +40° C. in an organic solvent such as a chlorine-containing solvent (for example dichloromethane, dichloroethane, chloroform), an ether (for example tetrahydrofuran, dioxane), an ester (for example ethyl acetate), an amide (for example dimethylacetamide, dimethylformamide), or a ketone (for example acetone) or in a mixture of these solvents, in the presence of an acid acceptor such as a nitrogen-containing organic base such as for example pyridine, dimethylaminopyridine, N-methylmorpholine or a trialkylamine (in particular triethylamine) or such as an epoxide (for example propylene oxide). It is also possible to carry out the procedure in the presence of a condensation agent such as a carbodiimide, [for example dicyclohexylcarbodiimide or 1-(3-dimethylaminopropyl)- 3-ethylcarbodiimide], N,N'-carbonyldiimidazole or 2-ethoxy-1-ethoxycarbonyl-1,2-dihydroquinoline or alternatively in a dilute organic medium in the presence of an alkaline condensation agent such as sodium bicarbonate, and where appropriate the amide obtained is then converted to an amidine as defined above.

The conversion of the amide of general formula (X) to an amidine for which X is an NH radical is carried out by preparing the isoindolium derivative of general formula:

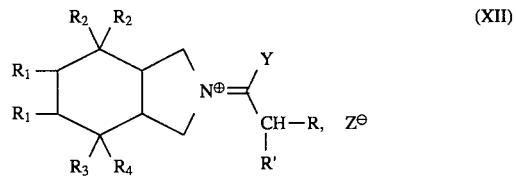

in which R, R', $R_1$, $R_2$, $R_3$ and $R_4$ are defined as above, Y represents a chlorine atom, a methoxy or ethoxy radical and $Z^-$ represents a chloride, tetrafluoroborate, fluorosulphonate, trifluoromethylsulphonate, methyl sulphate or ethyl sulphate ion, followed by reaction of ammonia with the isoindolium derivative.

It is understood that when $R_3$ is a hydroxyl, Y is other than a chlorine atom.

The preparation of the isoindolium derivative of general formula (XII) in which Y is a chlorine atom or a methoxy or ethoxy radical, is carried out by reaction of a reagent such as phosgene, phosphorus oxychloride, phosphorus pentachloride, thionyl chloride, oxalyl chloride, trichloromethyl chloroformate, triethyl- or trimethyloxonium tetrafluoroborate, methyl or ethyl triflate, methyl or ethyl fluorosulphonate or methyl or ethyl sulphate. The reaction is carried out in a chlorine-containing solvent (for example dichloromethane, dichloroethane) or in an aromatic hydrocarbon (for example toluene) at a temperature between 0° C. and the reflux temperature of the reaction mixture. The reaction of ammonia with the derivative of general formula (XII) is carried out in an anhydrous organic solvent such as a chlorine-containing solvent (for example dichloromethane, dichloroethane) in an alcohol-chlorine-containing solvent mixture, in an ether (for example tetrahydrofuran), in an ester (for example ethyl acetate), in an aromatic solvent (for example toluene) or in a mixture of these solvents, at a temperature between −20° C. and the reflux temperature of the reaction mixture.

It is not essential to isolate the isoindolium derivative of general formula (XII) in order to use it in this reaction.

The isoindole derivatives of general formula (X) for which X is an imino radical, may also be obtained from the isoindole derivative according to the invention, by reaction of a product of general formula:

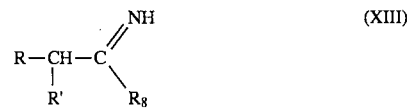

optionally in the form of a salt, in which R and R' are defined as above and $R_6$ represents an alkoxy radical containing 1 to 4 carbon atoms in a linear or branched chain or a methylthio, ethylthio, benzylthio or alkoxycarbonylmethylthio radical.

The reaction is carried out using the derivative of general formula (XIII), which is optionally prepared in situ, in an organic solvent such as a chlorine-containing solvent (for example dichloromethane, dichloroethane), an ether (for example tetrahydrofuran), an aromatic hydrocarbon (for example toluene) or a nitrile for example acetonitrile, at a temperature between 0° C. and the reflux temperature of the reaction mixture.

It is understood that should the radicals R and/or R' of the product of general formula (XIII) carry substituents which may interfere with the reaction, these substituents should be protected beforehand.

The acids of general formula (XI) are prepared according to known methods or according to the methods described in the examples below, or by analogy with these methods.

The new isoindole derivatives of general formula (I) and the products of general formula (X) to which they lead may be purified, where appropriate, by physical methods such as crystallization or chromatography.

Where appropriate, the new derivatives of general formula (I), as well as the products of general formula (X) to which they lead and for which the symbols R and/or R' contain amino or alkylamino substituents and/or X represents an NH radical, may be converted to the addition salts with acids. As examples of addition salts with pharmaceutically acceptable acids, there may be mentioned the salts formed with inorganic acids (hydrochlorides, hydrobromides, sulphates, nitrates, phosphates) or with organic acids (succinates, fumarates, tartrates, acetates, propionates, maleates, citrates, methanesulphonates, p-toluenesulphonates, isothionates, or with substituted derivatives of these compounds).

The new isoindole derivatives of general formula (X) antagonize the effects of substance P and thus may find an application in the fields of analgesia, inflammation, asthma, allergies, on the central nervous system, on the cardiovascular system, as antispasmodic, or on the immune system, as well as in the domain of the stimulation of lachrymal secretions.

Indeed, the products according to the invention exhibit an affinity for substance P receptors at doses of between 5 and 2000 nM according to the technique described by C. M. Lee et al., Mol. Pharmacol., 23, 563–69 (1983).

Furthermore, it has been demonstrated, using various products, that it is a substance P-antagonizing effect. In the technique described by S. Rosell et al., Substance P, Ed. by US Von Euler and B. Pernow, Raven Press, New York (1977), pages 83 to 88, the products studied proved to be active at doses of between 20 and 1000 nM.

Substance P is known to be involved in a certain number of pathological domains:

Agonists and antagonists of substance P, A. S. Dutta Drugs of the futur, 12 (8), 782 (1987);

Substance P and pain: an updating, J. L. Henry, TINS, 3(4), 97 (1980);

Substance P in inflammatory reactions and pain, S. Rosell, Actual. Chim. Ther., 12th series, 249 (1985);

Effects of Neuropeptides on Production of Inflammatory Cytokines by Human Monocytes, M. Lotz et al., Science, 241, 1218 (1988);

Neuropeptides and the pathogenesis of allergy, Allergy, 42, 1 to 11 (1987);

Substance P in Human Essential Hypertension, J. Cardiovascular Pharmacology, 10 (suppl. 12), 5172 (1987).

Moreover, the isoindole derivatives of general formula (X) are not toxic, they proved to be nontoxic in mice by the subcutaneous route at a dose of of 40 mg/kg or by the oral route at a dose of 100 mg/kg.

The perhydroisoindole derivatives of general formula (I) for which:

the radicals $R_1$ are hydrogen atoms, the symbols $R_2$ are identical and represent phenyl radicals, the symbol $R_3$ represents a fluorine or chlorine atom or a hydroxyl radical, and the symbol $R_4$ represents a hydrogen atom or, together with $R_3$, represents a fluorine atom, are of particular interest.

And among these products, the following products are more particularly advantageous:

7,7-diphenyl-4-perhydroisoindolol, 4,4-diphenyl-7-fluoroperhydroisoindole, 4,4-diphenyl-7,7-difluoroperhydroisoindole, 7-chloro-4,4-diphenylperhydroisoindole, in their stereoisomeric forms as well as mixtures thereof and their salts.

EXAMPLES

The following examples, which are given with no limitation being implied, illustrate the present invention.

In the examples below, it is understood, unless specifically stated, that the proton NMR spectra were established at 250 MHz in dimethyl sulphoxide; the chemical shifts are expressed in ppm.

Example 1

A solution of 7.18 g of sodium borohydride in 500 cm³ of methanol supplemented with 20 drops of a concentrated solution of sodium hydroxide is added over 90 minutes to a solution, cooled to 5° C., of 100 g of (3aR, 7aR)-7,7-diphenyl-4-perhydroisoindolone in 1000 cm³ of absolute methanol. After stirring for 2.5 hours between 5 and 10° C., the crystals formed are drained and taken up in 900 cm³ of water and 1000 cm³ of ethyl ether. The solution is filtered and alkalized with 15 cm³ of a 4N solution of sodium hydroxide and then stirred for 2 hours at 5° C. The crystals formed are drained, washed with ethyl ether and dried to give 28.8 g of (3aR, 7S, 7aR)-7,7-diphenyl-4-perhydroisoindolol in the form of white crystals; melting point 205° C., $[\alpha]_D^{20} = -230°$ (c=1, CHCl$_3$).

(3aR, 7aR)-7,7-Diphenyl-4-perhydroisoindolone hydrochloride may be prepared in the following manner:

500 cm³ of 4N aqueous sodium hydroxide are slowly added with stirring to a suspension of 200 g of (3aRS, 7aRS)-7,7-diphenyl-4-perhydroisoindolone hydrochloride in 2000 cm³ of ethyl acetate; the stirring is continued until dissolution of the starting product. The organic solution is washed with 250 cm³ of distilled water, with 250 cm³ of a saturated aqueous solution of sodium chloride, dried over magnesium sulphate and filtered. A solution of 92.8 g of L(+)-mandelic acid in 1000 cm³ of ethyl acetate is added with stirring to the solution thus obtained; after stirring for 4 hours, the crystals obtained are drained, washed with 250 cm³ of ethyl acetate (twice) and dried. The crystals are taken up in 2000 cm³ of distilled water; the mixture is refluxed with stirring for 15 minutes; the insoluble crystals are drained, washed with 100 cm³ of distilled water (twice) and dried. They are recrystallized from a mixture of 1100 cm³ of acetonitrile and 500 cm³ of distilled water; the crystals obtained are drained, washed with 40 cm³ of acetonitrile (3 times) and dried. 80 g of (3aR, 7aR)-7,7-diphenyl-4-perhydroisoindolone (L)-mandelate are obtained; $[\alpha]_D^{20} = -164°$ (c=1, methanol).

400 cm³ of 1N aqueous sodium hydroxide and 600 cm³ of ethyl acetate are added to 80 g of (3aR, 7aR)-7,7-diphenyl-4-perhydroisoindolone (L)-mandelate; the mixture is stirred at room temperature until dissolution of the starting product; the organic solution is washed with 250 cm³ of distilled water, with 250 cm³ of a saturated aqueous solution of sodium chloride, dried over magnesium sulphate and filtered; it is acidified, with stirring, by the addition of 30 cm³ of 9N hydrochloric acid; the crystals obtained are drained, washed with 50 cm³ of ethyl acetate (twice), with 50 cm³ of isopropyl oxide and dried. 52.3 g of (3aR, 7aR)-7,7-diphenyl-4-perhydroisoindolone hydrochloride is obtained; melting point 270° C., with decomposition; $[\alpha]_D^{20} = -282°$ (c=0.5, methanol).

(3aRS, 7aRS)-7,7-Diphenyl-4perhydroisoindolone hydrochloride may be prepared in the following manner:

150 g of (3aRS, 7aRS)-2-benzyl-7,7-diphenyl-4-perhydroisoindolone, 1500 cm³ of methanol and 450 cm³ of 1N hydrochloric acid are added to 15 g of 10% palladium on carbon; the reaction mixture is hydrogenated, with stirring, at room temperature and under atmospheric pressure. The theoretical volume of hydrogen is absorbed after reacting for 5 hours; the reaction mixture is filtered and then concentrated to dryness under reduced pressure (2.7 kPa); the residue is crystallized from 200 cm³ of ethanol; the crystals obtained are drained, washed with 50 cm³ of ethanol and dried. 110 g of (3aRS, 7aRS)-7,7-diphenyl-4-perhydroisoindolone hydrochloride are obtained; melting point 270° C., with decomposition.

Proton NMR spectrum: 2.03 (Mt, 1H, 1H of H in 5 or 6); 2.3 (Mt, 1H, 1H of —H in 5 or 6); 2.48 (DD, partially masked, 1H of —CH₂ in 1); 2.69 (DD, 1H, 1H of —CH₂—in 1); 2.8 (Mt, 2H, —CH₂—in 6 or 5); 3.34 (DD, partially masked, 1H of —CH₂—in 3); 3.5 (Mt, 1H, —CH—in 3a); 3.82 (DD, 1H, 1H of —CH₂—in 3); 3.95 (Mt, 1H, —CH—in 7a); 7.15 to 7.65 (Mt, 10H, aromatics); 9.43 (Mf, 2H, —NH₂⁺).

Infrared spectrum (KBr) characteristic bands in cm⁻¹: 3600–3300, 3100–3000, 3000–2850, 3100–2400, 1715, 1595, 1580, 1495, 1470, 1445, 775, 750, 705.

(3aRS, 7aRS)-2-Benzyl-7,7-diphenyl-4-perhydroisoindolone may be prepared in the following manner:

5 drops of trifluoroacetic acid are added to a solution of 155 g of 4,4-diphenyl-2-cyclohexen-1-one and 202 cm³ of N-butoxymethyl-N-trimethylsilylmethylbenzylamine in 1000 cm³ of dry dichloromethane and the reaction mixture is refluxed for 45 minutes. 50 cm³ of N-butoxymethyl-N-trimethylsilylmethylbenzylamine and 3 drops of trifluoroacetic acid are added and the mixture is further stirred for 45 minutes under reflux before again adding 25 cm³ of N-butoxymethyl-N-trimethylsilylmethylbenzylamine and 3 drops of trifluoroacetic acid. The reaction mixture is stirred under reflux for 45 minutes and then treated with 50 g of potassium carbonate, filtered and concentrated to dryness under reduced pressure (2.7 kPa). The residue is dissolved in 200 cm³ of isopropyl oxide and the solution is cooled to 0° C. for 1 hour. The crystals are drained, washed twice with 15 cm³ of isopropyl oxide and dried to give 193 g of (3aRS, 7aRS)-2-benzyl-7,7-diphenyl-4-perhydroisoindolone in the form of white crystals; melting point 132° C.

N-Butoxymethyl-N-trimethylsilylmethylbenzylamine may be prepared according to the method of Y. Terao et al., Chem. Pharm. Bull., 33, 2762 (1985).

Example 2

A solution of 1 g of sodium borohydride in 200 cm³ of methanol is added dropwise over 40 minutes to a solution, cooled to +4° C., of 17.8 g of (3aR, 7aR)-7,7-diphenyl-2-tert-butyloxycarbonyl- 4-perhydroisoindolone in one litre of methanol, followed by 10 drops of lye. The reaction mixture is stirred for 3 hours at +4° C. and then 2 cm³ of a 0.1N aqueous solution of hydrochloric acid are added and the mixture is concentrated to dryness under reduced pressure (2.7 kPa). The residue is dissolved in 350 cm³ of dichloromethane, washed with 100 cm³ of water and then with 50 cm³ of a saturated solution of sodium chloride, dried over magnesium sulphate and concentrated to dryness under reduced pressure (2.7 kPa). The residue is crystallized from 40 cm³ of ethyl ether. The crystals obtained are drained and dried. 8.4 g of (3aR, 4S, 7aR)-7,7-diphenyl-2-tert-butyloxycarbonyl- 4-perhydroisoindolol are obtained in the form of white crystals; melting point 190° C. The crystallization mother liquors are concentrated to dryness under reduced pressure (2.7 kPa). The residue is chromatographed on a silica gel column (particle size 0.04–0.06 mm, diameter 4 cm, height 33 cm), eluting under a nitrogen pressure of 0.4 bar with a dichloromethane and methanol mixture (96/4 by volume) and collecting fractions of 20 cm³. Fractions 18 to 21 are pooled and concentrated to dryness under reduced pressure (2.7 kPa). 1.88 g of (3aR, 4R,7aR)-7,7-diphenyl-2-tert-butyloxycarbonyl- 4-perhydroisoindolol are obtained in the form of a white meringue. Fractions 26 to 31 are pooled and concentrated to dryness under reduced pressure (2.7 kPa). The residue is crystallized from 5 cm³ of ethyl ether. 2.88 g of (3aR, 4S, 7aR)-7,7-diphenyl-2-tert-butyloxycarbonyl- 4-perhydroisoindolol are additionally obtained in the form of white crystals; melting point 190° C.

(3aR, 7aR)-7,7-Diphenyl-2-tert-butyloxycarbonyl-4-perhydroisoindolone may be obtained in the following manner:

0.74 g of 4-dimethylaminopyridine and 14.7 g of di-tert-butyl dicarbonate are successively added to a solution of 20 g of (3aR, 7aR)-7,7-diphenyl-4-perhydroisoindolone hydrochloride in 100 cm³ of dry dichloromethane and 6.17 cm³ of triethylamine. The reaction mixture is stirred for 24 hours at room temperature and then washed with an aqueous solution of citric acid and then with an aqueous solution of sodium hydrogen carbonate, dried over magnesium sulphate, filtered and concentrated to dryness under reduced pressure (2.7 kPa). The residue is crystallized from 90 cm³ of ethyl ether. The crystals are drained, washed with 10 cm³ of ethyl ether and then dried. 14.1 g of (3aR, 7aR)-7,7-diphenyl-2-tert-butyloxycarbonyl-4-perhydroisoindolone are obtained in the form of white crystals; melting point 119° C.

40 cm³ of a 6.3 N solution of hydrochloric dioxane are added to a solution of 2 g of (3aR, 4S, 7aR)7,7-diphenyl-2-tert-butyloxycarbonyl-4-perhydroisoindolol in 20 cm³ of dioxane and the mixture is stirred at room temperature for 5 hours. The reaction mixture is concentrated to dryness under reduced pressure (2.7 kPa), triturated in acetonitrile, filtered and dried. 1.57 g of (3aR, 4S, 7aR)-7,7-diphenyl-4-perhydroisoindolol hydrochloride are obtained in the form of white crystals; melting point 266° C.

Example 3

(3aR, 4R,7aR)-7,7-Diphenyl-4-perhydroisoindolol hydrochloride may be prepared by hydrogenation of a suspension of 0.70 g of (3aR, 4R,7aR)-2-benzyl-7,7-diphenyl-4-perhydroisoindolol in 30 cm³ of methanol and 2.0 cm³ of 1N hydrochloric acid at atmospheric pressure for 20 hours at 20° C. in the presence of 0.12 g of 20% palladium hydroxide on carbon black. The reaction mixture is filtered, concentrated to dryness under reduced pressure (2.7 kPa), and the oil obtained is concreted with ethyl ether. The suspension is filtered, the solid drained and dried under reduced pressure (2.7 kPa). 0.52 g of (3aR, 4R,7aR)-7,7-diphenyl-4-perhydroisoindolol hydrochloride is obtained in the form of a white solid; melting point 220° C. (with decomposition).

Infrared spectrum (characteristic bands, cm$^{-1}$): 3400, 3090, 3050, 3025, 3000–2800, 1600, 1580, 1495, 1465, 985, 750, 700.

Proton NMR spectrum (DMSO-d$_6$, main signals): 1.06 (broad t, J=14, 1H, H in 5); 1.66 (broad d, J=14, 1H, H in 5); 2.17 (broad d, J=14, 1H, CH$_2$ in 6); 3.8 (broad s, 1H, H in 4); 5.3 (mf, 1H, OH); 7.05 to 7.45 (mt, 10H, aromatics); 8.4 and 9.43 (mf, 2H, NH$_2^+$).

(3aR, 4R,7aR)-2-Benzyl-7,7-diphenyl-4-perhydroisoindolol may be prepared in the following manner:

4.0 cm$^3$ of a 1M solution of lithium tri-sec-butyl borohydride in tetrahydrofuran is added over 5 minutes to a solution, cooled to 0° C., of 1.3 g of (3aR, 7aR)-2-benzyl-7,7-diphenyl-4-perhydroisoindolone in 6.0 cm$^3$ of tetrahydrofuran. After stirring for 3 hours at 0° C., the reaction mixture is again supplemented with 0.5 cm$^3$ of the 1M solution of borohydride. After 1 hour at 0° C. and the addition of 50 cm$^3$ of water and 50 cm$^3$ of ethyl acetate, the organic phase is decanted, washed with 20 cm$^3$ of water, dried over magnesium sulphate and concentrated to dryness under reduced pressure (2.7 kPa). The oil obtained is crystallized from 30 cm$^3$ of diisopropyl oxide, the crystals are drained and dried under reduced pressure (2.7 kPa). 0.70 g of (3aR, 4R,7aR)-2-benzyl-7,7-diphenyl-4-perhydroisoindolol is obtained in the form of white crystals; melting point 154° C.

(3aR, 7aR)-2-Benzyl-7,7-diphenyl-4-perhydroisoindolone may be prepared in the following manner:

7.9 cm$^3$ of benzyl bromide are added to a solution, cooled to 0° C., of 21.7 g of (3aR,7aR)-7,7-diphenyl-4-perhydroisoindolone hydrochloride in 300 cm$^3$ of dichloromethane and 18.5 cm$^3$ of triethylamine. After stirring for 1 hour at 0° C. and 2 hours at 20° C., the reaction mixture is washed with 50 cm$^3$ of water, dried over magnesium sulphate and concentrated to dryness under reduced pressure (2.7 kPa). The residue is chromatographed on a silica gel column (0.04–0.06 mm, diameter 5 cm, height 40 cm), eluting under a nitrogen pressure of 0.6 bar with an ethyl acetate and cyclohexane mixture (75/25 by volume) and collecting fractions of 250 cm$^3$. Fractions 3 to 6 are pooled and concentrated to dryness under reduced pressure (2.7 kPa). 22.1 g of (3aR, 7aR)-2-benzyl-7,7-diphenyl-4-perhydroisoindolone are obtained in the form of a white solid; melting point 124° C. [α]$^{20}$=−279° C.

Example 4

A solution of 0.37 cm$^3$ of 4-trifluorothiomorpholine in 10 cm$^3$ of dry dichloromethane is added to a solution, cooled to +5° C. of 1.0 g of (3aR, 4R,7aR)-2-tert-butyloxycarbonyl-7,7-diphenyl-4-perhydroisoindolol in 20 cm$^3$ of dry dichloromethane. After stirring for 2 hours at +5° C., the reaction mixture is washed with 20 cm$^3$ of a 5% aqueous solution of sodium bicarbonate and then dried over magnesium sulphate and concentrated to dryness under reduced pressure (2.7 kPa). The residue is chromatographed on a silica gel column (particle size 0.04 mm–0.06 mm, diameter 2.4 cm, height 35 cm), eluting under a nitrogen pressure at 0.8 bar with a cyclohexane and ethyl acetate mixture (90/10 by volume) and collecting fractions of 25 cm$^3$. Fractions 25 to 34 are pooled and concentrated to dryness. 0.27 g of (3aR, 7S, 7aR)-4,4-diphenyl-7-fluoro- 2-tert-butyloxycarbonylperhydroisoindole is obtained in the form of a white meringue.

Infrared spectrum (KBr, characteristic bands, cm$^{-1}$): 3090, 3060, 3030, 2975, 2930, 2875, 1695, 1595, 1580, 1495, 1450, 1405, 1365, 1175, 755, 730, 700.

By carrying out the procedure as in Example 8 below, using 0.5 g of (3aR, 7S, 7aR)-4,4-diphenyl-7-fluoro- 2-tert-butyloxycarbonylperhydroisoindole, 0.35 g of (3aR, 7S, 7aR)-4,4-diphenyl-7-fluoroperhydroisoindole hydrochloride is obtained in the form of a grey solid.

Infrared spectrum (KBr, characteristic bands, cm$^{-1}$): 3420, 3090, 3050, 3025, 2970, 2800–2250, 1590, 1580, 1495, 1460, 1445, 1060, 750, 730, 700.

Example 5

A solution of 3.5 cm$^3$ of morpholinosulphur trifluoride in 50 cm$^3$ of dichloromethane is added to a solution, cooled to +5° C., of 9.4 g of (3aR, 4S, 7aR)-7,7-diphenyl- 2-tert-butyloxycarbonyl-4-perhydroisoindolol in 250 cm$^3$ of dry dichloromethane. The reaction mixture is stirred for 4 hours at +5° C. and then diluted with 300 cm$^3$ of dichloromethane, washed with 250 cm$^3$ of an aqueous solution of sodium hydrogen carbonate, dried over magnesium sulphate, filtered and concentrated to dryness under reduced pressure (2.7 kPa). The residue is chromatographed on a silica gel column (particle size 0.04–0.06 mm, diameter 3.5 cm, height 42 cm), eluting under a nitrogen pressure of 0.5 bar with a cyclohexane and ethyl acetate mixture (90/10 by volume) and collecting fractions of 120 cm$^3$. Fractions 13 to 17 are pooled and concentrated to dryness under reduced pressure (2.7 kPa). The residue is crystallized from cyclohexane. 2.55 g of (3aR, 7R,7aR)-4,4-Diphenyl-7-fluoro- 2-tert-butyloxycarbonylperhydroisoindole are obtained in the form of white crystals; melting point 202° C.

40 cm$^3$ of a 6.3N solution of hydrochloric dioxane are added to a solution of 3.7 g of (3aR, 7R,7aR)-4,4-diphenyl-7-fluoro-2-tert-butyloxycarbonylperhydroisoindole in 40 cm$^3$ of dioxane and the mixture is stirred at room temperature for 2 hours. The reaction mixture is concentrated to dryness under reduced pressure (2.7 kPa), triturated in diisopropyl oxide, filtered and dried. 3.1 g of (3aR, 7R,7aR)-4,4-diphenyl-7-fluoroperhydroisoindole hydrochloride are obtained in the form of white crystals; melting point 200° C. with decomposition.

Example 6

1.3 g of calcium carbonate and then 2 g of phosphorus pentachloride are successively added to a solution, cooled to +4° C., of 1 g of (3aR, 4S, 7aR)-7,7-diphenyl-2-tert-butyloxycarbonyl-4-perhydroisoindolol in 60 cm$^3$ of chloroform, and the mixture is stirred at room temperature for 20 hours. The reaction mixture is then filtered, diluted with 80 cm$^3$ of chloroform, washed twice with 80 cm$^3$ of water, dried over magnesium sulphate and concentrated to dryness under reduced pressure (2.7 kPa). The residue is chromatographed on a silica gel column (particle size 0.04–0.06 mm, diameter 2.5 cm, height 34 cm), eluting under a nitrogen pressure of 0.4 bar with a cyclohexane and ethyl acetate mixture (30/70 by volume) and collecting fractions of 20 cm$^3$. Fractions 7 to 10 are pooled and concentrated to dryness under reduced pressure (2.7 kPa). 0.44 g of (3aR, 7R,7aR)-7-chloro-2-chlorocarbonyl- 4,4-diphenylperhydroisoindole is obtained in the form of a white solid.

Infrared spectrum (CCl$_4$ solution, characteristic bands, cm$^{-1}$): 3090, 3065, 3035, 2930, 2855, 1745, 1600, 1585, 1495, 1450, 700.

A solution of 0.4 g of (3aR, 7R,7aR)-7-chloro-2-chlorocarbonyl- 4,4-diphenylperhydroisoindole in 6 cm$^3$ of a 1N aqueous solution of hydrochloric acid and 14 cm$^3$ of tetrahydrofuran is heated with stirring at 80° C. for 9 hours. The reaction mixture is concentrated to dryness under reduced pressure (2.7 kPa). 0.35 g of (3aR, 7R,7aR)-7-chloro-4,4-diphenylperhydroisoindole hydrochloride is obtained in the form of a white solid.

Infrared spectrum (KBr, characteristic bands, cm$^{-1}$): 3055, 3025, 3000, 2250, 1600, 1495, 1580, 1460, 1445, 1435, 760, 750, 735, 700.

Example 7

A solution of 1 g of (3aR, 4S, 7aR)-2-tert-butyloxycarbonyl- 7,7-diphenyl-4-perhydroisoindolol in 10 cm$^3$ of thionyl chloride is stirred for 3 hours at 80° C. The reaction mixture is then concentrated to dryness under reduced pressure (2.7 kPa). 1.03 g of (3aR, 7S, 7aR)-2-tert-butyloxycarbonyl-7-chloro-4,4-diphenylperhydroisoindole are obtained in the form of a solid which is used in the crude state in the following test.

10 cm$^3$ of a 6.3N solution of hydrochloric acid in dioxane are added to a solution of 1.03 g of (3aR, 7S, 7aR)-2-tert-butyloxycarbonyl-7-chloro-4,4-diphenylperhydroisoindole in 5 cm$^3$ of dioxane. The reaction mixture is stirred at room temperature for 2 hours and then concentrated to dryness under reduced pressure (2.7 kPa). 0.84 g of (3aR, 7S, 7aR)-7-chloro-4,4-diphenylperhydroisoindole hydrochloride is obtained in the form of a solid which is used in the crude state in the following test.

Example 8

A solution of 5.0 g of (3aRS, 7aRS)-2-tert-butyloxycarbonyl- 7,7-diphenyl-4-perhydroisoindolone in 30 cm$^3$ of dry dichloromethane is added to a solution of 3.4 cm$^3$ of diethylaminosulphur trifluoride in 20 cm$^3$ of dry dichloromethane. After stirring for 5 hours under reflux and for 20 hours at 20° C. the reaction mixture is washed with 50 cm$^3$ of a saturated aqueous solution of sodium bicarbonate and with 50 cm$^3$ of water and then dried over magnesium sulphate and concentrated to dryness. The residue is chromatographed on a silica gel column (particle size 0.04–0.06 mm, diameter 2.8 cm, height 35 cm), eluting under a nitrogen pressure of 0.8 bar with a cyclohexane and ethyl acetate mixture (95/5 followed by 90/10 by volume) and collecting fractions of 25 cm$^3$. Fractions 24 to 52 are pooled and concentrated to dryness under reduced pressure (2.7 kPa). The residue is crystallized in ethyl acetate and diisopropyl oxide, the crystals are drained and dried. 1.80 g of (3aRS, 7aRS)-2-tert-butyloxycarbonyl-4,4-diphenyl- 7,7-difluoroperhydroisoindole are obtained in the form of white crystals; melting point 162° C.

20 cm$^3$ of dioxane and 20 cm$^3$ of 6.3N hydrochloric acid are added to 1.8 g of (3aRS, 7aRS)-2-tert-butyloxycarbonyl-4,4-diphenyl-7,7difluoroperhydroisoindole. After stirring for 20 hours at room temperature, the white suspension obtained is concentrated to dryness at 40° C. under reduced pressure (2.7 kPa). The residue is washed with diisopropyl oxide, the solid obtained is drained and then dried. 1.51 g of (3aRS, 7aRS)-4,4-diphenyl-7,7-difluoroperhydroisoindole hydrochloride are obtained in the form of a white solid.

Infrared spectrum (KBr, characteristic bands, cm$^{-1}$): 3090, 3050, 3025, 2965, 2935, 2900, 2800–2250, 1595, 1580, 1495, 1465, 1445, 760, 730, 700.

Proton NMR spectrum (DMSO-d$_6$+CF$_3$COOD): 1.2–1.55 and 2.12 (2 mt, 2×1H, CH$_2$ in 6); 3–3.3 (mt, 1H, H in 7a); 3.58 (mt, 2H, CH$_2$ in 1); 3.76 (mt, 1H, H in 3a); 7.1 at 7.5 (mt, 10H, aromatics).

Example 9

A solution of 4.87 g of (3aR, 7S, 7aR)-2-t-butoxycarbonyl- 4,4-diphenyl-7trifluoromethylsulphonyloxyperhydroisoindole in 150 cm$^3$ of dry difluoromethane is treated with 22.6 cm$^3$ of a 1M solution of tetrabutylammonium fluoride in tetrahydrofuran and then stirred for 17 hours at 20° C and concentrated to dryness under reduced pressure (2.7 kPa). The residue is chromatographed on a silica gel column (particle size 0.2–0.063 mm, diameter 4.5 cm, height 35 cm), eluting under a nitrogen pressure of 0.4 bar with a cyclohexane and ethyl acetate mixture (75/25) and collecting fractions of 20 cm$^3$. Fractions 28 to 38 are pooled and concentrated to dryness under reduced pressure (2.7 kPa) to give 1.44 g of (3aR, 7R,7aR)-2-t-butoxycarbonyl-4,4-diphenyl-7-fluoroperhydroisoindole in the form of white crystals; melting point 200° C., [α]$_D^{20}$=–225° C. (c=1, CHCl$_3$).

A solution of 2.25 g of (3aR, 7R,7aR)-2-t- butoxycarbonyl-4,4-diphenyl-7-fluoroperhydroisoindole in 25 cm$^3$ of dioxane is treated with a 5.8N solution of hydrochloric acid in dioxane and stirred for 2 hours at 20° C. and then concentrated to dryness under reduced pressure (2.7 kPa). The residue is concreted by adding 100 cm$^3$ of isopropyl oxide, the solid is filtered and dried to give 1.8 g of (3aR, 7R,7aR)-4,4-diphenyl-7-fluoroperhydroisoindole hydrochloride in the form of a cream-colored powder.

Proton NMR spectrum (DMSO-d$_6$): 1.0–1.35 (mt, 1H of CH$_2$ in 6); 4.9 (broad d, J=50, 1H, CHF); 7.1 to 7.5 (mt, 14H, aromatics); 9.05 and 9.9 (2 mf, 2×1H, NH$_2^+$).

(3aR, 7S, 7aR)-2-t-Butoxycarbonyl-4,4-diphenyl-7-trifluoromethylsulphonyloxyperhydroisoindole may be obtained in the following manner:

1.5 cm$^3$ of pyridine are added to a solution, cooled to –30° C., of 6.7 g of (3aR, 4S, 7aR)-2-t-butoxycarbonyl- 7,7-diphenyl-4-perhydroisoindolol in 100 cm$^3$ of dry dichloromethane, followed over 10 minutes by a solution of 3.2 g of trifluoromethanesulphonic anhydride in 25 cm$^3$ of dry dichloromethane. The reaction mixture is stirred for 2 hours at –30° C. and then diluted with 250 cm$^3$ of water and 100 cm$^3$ of dichloromethane. The organic phase is washed with 200 cm$^3$ of a saturated solution of sodium bicarbonate and with 200 cm$^3$ of a saturated solution of sodium chloride and then dried and concentrated to dryness under reduced pressure (2.7 kPa) to give 8.6 g of (3aR, 7S, 7aR)-2-t-butoxycarbonyl-4,4-diphenyl-7-trifluoromethylsulphonyloxyperhydroisoindole in the form of a yellow meringue which is used as it is in subsequent stages of the synthesis.

(3aR, 4S, 7aR)-2-t-Butoxycarbonyl-7,7-diphenyl-4-perhydroisoindolol may be obtained in the following manner:

10.55 g of di-tert-butyl dicarbonate are added to a solution of 13 g of (3aR, 4S, 7aR)-7,7-diphenyl-4-perhydroisoindolol and 0.5 g of 4-dimethylaminopyridine in 450 cm$^3$ of dichloromethane. After stirring for 2 hours at 25° C., the reaction mixture is concentrated to dryness under reduced pressure (2.7 kPa) and the residue is crystallized in 50 cm³ of ethyl ether. 9 g of (3aR, 4S, 7aR)-2-t-butoxycarbonyl- 7,7-diphenyl-4-perhydroisoindolol are obtained in the form of white crystals; melting point 190° C.

The products according to the invention may be used for the preparation of the isoindole derivatives of general formula (X) as in the examples of use below.

Example of use 1

A solution of 0.5 g of 1-(3-dimethylaminopropyl)-3-ethylcarbodiimide in 50 cm³ of dry dichloromethane is added over 10 minutes to a solution, cooled to +4° C., of 0.72 g of (3aR, 7R,7aR)-4,4-diphenyl- 7-fluoroperhydroisoindole hydrochloride, 0.5 g of 2-(3-dimethylaminopropoxy)phenylacetic acid, 0.03 g of 1-hydroxybenzotriazole in 75 cm³ of dichloromethane, followed by 0.37 cm³ of diisopropylethylamine. The reaction mixture is stirred for 3 hours at 0° C. and then washed twice with 50 cm³ of water and twice with 50 cm³ of a saturated solution of sodium chloride. The organic phase is dried over magnesium sulphate and concentrated to dryness under reduced pressure (2.7 kPa). The residue is taken up in 21 cm³ of 0.1N hydrochloric acid, 50 cm³ of diethyl ether and 30 cm³ of water. The aqueous phase is separated and freeze-dried to give 0.85 g of (3aR, 7R,7aR)-2-([2-(3-dimethylaminopropoxy)phenyl]acetyl)-4,4-diphenyl- 7-fluoroperhydroisoindole hydrochloride in the form of a white freeze-dried product.

Infrared spectrum (KBr, characteristic bands, cm⁻¹): 3060, 3030, 2960, 2890, 2800, 2200, 1635, 1605, 1495, 1460, 1445, 1250, 755, 705.

Proton NMR spectrum (DMSO-$d_6$) (at room temperature, a mixture of the two rotamers is observed): 0.95–1.35 and 1.8–2.1 (2mt, 2×1H, $CH_2$ in 6): 2.6–2.8 (mt, 6H, $N(CH_3)_2$); 3.9 and 4.05 (2mt, 2×1H, $OCH_2$); 4.8 and 4.85 (broad 2d; J=50, 1H, CHF); 6.8 to 7.5 (mt, 14H, aromatics).

Example of use 2

0.04 g of hydroxybenzotriazole hydrate is added to a solution, cooled to +5° C., of 1 g of (3aR, 7R,7aR)-4,4-diphenyl-7-fluoroperhydroisoindole hydrochloride and 0.924 g of 2-{[3-(1-pyrrolidinyl)-2-propoxy]phenyl}acetic acid in 40 cm³ of dry dichloromethane, followed by 0.79 g of 1-(3-dimethylaminopropyl)-3-ethylcarbodiimide hydrochloride and 0.51 cm³ of diisopropylethylamine. After stirring for 2.5 hours at +5° C. and for 20 hours at 20° C., the reaction mixture is washed twice with 50 cm³ of water, dried over magnesium sulphate and then concentrated to dryness at 40° C. under reduced pressure (2.7 kPa). The residue is chromatographed on a silica gel column (particle size 0.04–0.06 mm, diameter 2.4 cm, height 31 cm), eluting under a nitrogen pressure of 0.5 bar with an ethyl acetate, acetic acid and water mixture (60/10/10 by volume) and collecting fractions of 25 cm³. Fractions 11 to 31 are pooled and concentrated to dryness under reduced pressure (2.7 kPa). The residue is taken up in 20 cm³ of dichloromethane, the solution is washed with 20 cm³ of a 1N aqueous solution of sodium hydroxide and then dried over magnesium sulphate and concentrated to dryness. This wash with a basic solution is repeated again. 0.68 g of (3aR, 7R,7aR)-2-{{[3-(1-pyrrolidinyl)- 2-propoxy]phenyl}acetyl}-4,4-diphenyl-7-fluoroperhydroisoindole is obtained in the form of a white solid.

Infrared spectrum (KBr, characteristic bands, cm⁻¹): 3085, 3055, 3035, 2950, 2875, 2785, 1640, 1600, 1495, 1455, 1440, 1245, 750, 700.

Proton NMR spectrum (DMSO-$d_6$ +$CF_3COOD$): 1.1–1.45 (mt, 1H, 1H in 6); 1.9 (mt, 4H, $2CH_2$ in 3 and 4 of pyrrolidino); 2.27 (mt, 1H, 1H in 5); 3.77 (d, J=10, 1H, H in 1); 4.03 (mt, 2H, $OCH_2$); 4.78 (broad d, J=50, 1H, CHF); 7.1 to 7.5 (mt, 14H, aromatics).

Example of use 3

By carrying out the procedure as in Example 9 below, using 0.16 g of 2-dimethylaminophenylacetic acid and 0.30 g of (3aR, 7S, 7aR)-4,4-diphenyl-7-fluoroperhydroisoindole hydrochloride, 0.11 g of (3aR, 7S, 7aR)-2-[(2-dimethylaminophenyl)acetyl]4,4-diphenyl-7-fluoroperhydroisoindole is obtained in the form of a white meringue.

Infrared spectrum (KBr, characteristic bands, cm⁻¹): 3090, 3060, 3030, 2940, 2875, 2825, 2770, 1645, 1595, 1580, 1495, 1450, 1420, 755, 730, 700.

Proton NMR spectrum (at room temperature, a mixture of two rotamers is observed): 2.35 and 2.58 (2s, 6H, $N(CH_3)_2$), 4.2–4.6 (mt, 1H, CHF ), 6.9–7.5 (mt, 14H, aromatics).

Example of use 4

0.28 cm³ of triethylamine and 0.32 g of carbonyldiimidazole are added to a solution, cooled to 4° C., of 0.57 g of (2-pyrrolidinophenyl)acetic acid hydrobromide in 20 cm³ of dry dichloromethane. The mixture is stirred for one hour at +4° C. and then a solution of 0.67 g of (3aR, 7R,7aR)-4,4-diphenyl-7-fluoroperhydroisoindole hydrochloride in 20 cm³ of dry dichloromethane and 0.28 cm³ of triethylamine is added. The reaction mixture is stirred at room temperature for 24 hours and then diluted with 100 cm³ of dichloromethane, washed twice with 50 cm³ of water, dried over magnesium sulphate, filtered and concentrated to dryness under reduced pressure (2.7 kPa). The residue is chromatographed on a silica gel column (particle size 0.04–0.06 mm, diameter 3.5 cm, height 38 cm), eluting under a nitrogen pressure of 0.5 bar with a cyclohexane and ethyl acetate mixture (70/30 by volume) and collecting fractions of 20 cm³. Fractions 26 to 54 are pooled and concentrated to dryness under reduced pressure (2.7 kPa). The residue is crystallized from an acetonitrile and diisopropyl oxide mixture (25/75 by volume). 0.16 g of (3aR, 7R,7aR)-4,4-diphenyl-7-fluoro-2-[( 2-pyrrolidinophenyl)acetyl]perhydroisoindole is obtained in the form of white crystals; melting point 170° C.

Example of use 5

0.17 g of carbonyldiimidazole is added to a solution, cooled to +4° C. of 0.19 g of (2-dimethylaminophenyl)acetic acid in 15 cm³ of dry dichloromethane. The mixture is stirred for one hour at 4° C. and then a solution of 0.35 g of (3aR, 7R,7aR)-7-chloro- 4,4-diphenylperhydroisoindole hydrochloride in 10 cm³ of dry dichloromethane is added followed by a solution of 0.15 cm³ of triethylamine in 10 cm³ of dry dichloromethane. The reaction mixture is stirred at room temperature for 20 hours and then diluted with 120 cm³ of dichloromethane, washed with 80 cm³ of water and then with a saturated aqueous solution of sodium chloride, dried over magnesium sulphate, filtered and concentrated to dryness under reduced pressure (2.7 kPa). The residue is chromatographed on a silica gel column (particle size 0.04–0.06 mm, diameter 2 cm, height 22 cm), eluting under a nitrogen pressure of 0.4 bar with an ethyl acetate and cyclohexane mixture (75/25 by volume) and collecting fractions of 20 cm³. Fractions 6 to 9 are pooled and concentrated to dryness under reduced pressure (2.7 kPa). The product, which is obtained in the form of a base, is converted to the hydrochloride by dissolving in 25 cm³ of ethyl ether, followed by the addition of 5 cm³ of a 3.2N solution of hydrochloric acid in ethyl ether, washing with ethyl ether and drying. 0.14 g of (3aR, 7R,7aR)-7-chloro-2-[(2-dimethylaminophenyl)acetyl]- 4,4diphenylperhydroisoindole hydrochloride is obtained in the form of white crystals; melting point 190° C.

Example of use 6

0.39 g of carbonyldiimidazole is added to a solution, cooled to +4° C., of 0.43 g of (2-dimethylaminophenyl)acetic acid in 15 cm³ of dry dichloromethane. The mixture is stirred for one hour at +4° C. and then a solution of 0.84 g of (3aR, 7S, 7aR)-7-chloro- 4,4-diphenylperhydroisoindole hydrochloride in 10 cm³ of dry dichloromethane is added followed by a solution of 0.34 cm³ of triethylamine in 10 cm³ of dry dichloromethane. The reaction mixture is stirred at room temperature for 20 hours, and then diluted with 100 cm³ of dichloromethane, washed with 50 cm³ of water and then with a saturated aqueous solution of sodium chloride, dried over magnesium sulphate, filtered and concentrated to dryness under reduced pressure (2.7 kPa). The residue is chromatographed on a silica gel column (particle size 0.04–0.06 mm, diameter 3 cm, height 23 cm), eluting under a nitrogen pressure of 0.4 bar with an ethyl acetate and cyclohexane mixture (25/75 by volume) and collecting fractions of 80 cm³. Fraction 2 is concentrated to dryness under reduced pressure (2.7 kPa). The product which is obtained in the form of a base is converted to the hydrochloride by dissolving in 4 cm³ of acetonitrile, followed by the addition of 6 cm³ of a 3.2N solution of hydrochloric acid in ethyl ether, washing with isopropyl ether and drying. 0.08 g of (3aR, 7S, 7aR)-7-chloro-2-[(2-dimethylaminophenyl)acetyl]- 4,4-diphenylperhydroisoindole hydrochloride is obtained in the form of a beige solid.

Infrared spectrum (KBr, characteristic bands, cm⁻¹): 3055, 3025, 2950, 1635, 1490, 1460, 1440, 760, 750, 700.

Proton NMR spectrum (DMSO-$d_6$) (at 403° K., a mixture of the two rotamers is observed, DMSO-$d_6$ +CF₃COOD, main signals): 3 and 3.13 (2s, 6H, N(CH₃)₂); 4.54 and 4.63 (2 mt, 1H, CHCl); 7 to 7.8 (mt, 14H, aromatics).

Example of use 7

0.32 g of carbonyldiimidazole is added to a solution, cooled to +4° C., of 0.36 g of (S)-2-(2-methoxyphenyl)propionic acid in 20 cm³ of dry dichloromethane. The mixture is stirred for one hour at +4° C. and then a solution of 0.67 g of (3aR, 7R,7aR)-4,4-diphenyl- 7-fluoroperhydroisoindole hydrochloride in 20 cm³ of dry dichloromethane and 0.28 cm³ of triethylamine is added. The reaction mixture is stirred at room temperature for 20 hours, diluted with 200 cm³ of dichloromethane and then washed with 50 cm³ of water, dried over magnesium sulphate, filtered and concentrated to dryness under reduced pressure (2.7 kPa). The residue is chromatographed on a silica gel column (particle size 0.04–0.06 mm, diameter 3 cm, height 20 cm), eluting under a nitrogen pressure of 0.4 bar with an ethyl acetate and cyclohexane mixture (60/40 by volume) and collecting fractions of 20 cm³. Fractions 10 to 15 are pooled and concentrated to dryness under reduced pressure (2.7 kPa). The residue is crystallized from 0.6 cm³ of isopropyl oxide. The crystals obtained are drained, washed with isopropyl oxide, and then dried. 0.19 g of (3aR, 7R,7aR)-4,4-diphenyl-7-fluoro-2-[(S)-2-(2methoxyphenyl)propionyl]perhydroisoindole is obtained in the form of white crystals; melting point 195° C.

(S)-2-(2-Methoxyphenyl)propionic acid may be obtained in the following manner:

(S)-2-(2-Methoxyphenyl)propionic acid may be prepared by analogy with the methods described by D. A. Evans et al., Tetrahedron, 44, 5525, (1988), according to the following procedure: 1.52 g of lithium hydroxide are added to a solution, cooled to +5° C., of 4.1 g of (4S, 5S)-4-methyl-5-phenyl-3-[(S)-2-(2-methoxyphenyl)-propionyl]- 2-oxazolidinone in 60 cm³ of tetrahydrofuran and 30 cm³ of water. The reaction mixture is stirred for 3 hours at this temperature and then, after re-equilibrating to room temperature, ethyl acetate is added, the mixture decanted and the aqueous phase is acidified with a 1N aqueous solution of hydrochloric acid, extracted with ethyl acetate and the organic phase is dried over magnesium sulphate and concentrated to dryness under reduced pressure (2.7 kPa). The solid obtained is recrystallized from hexane, drained and dried. 0.4 g of (S)-2-(2-methoxyphenyl)propionic acid is obtained in the form of white crystals; melting point 102° C. $[\alpha]_D^{20}$ =+84.6° (c=1; CHCl₃).

(4S,5S)-4-Methyl-5-phenyl-3-[(S)-2-(2-methoxyphenyl)propionyl]-2-oxazolidinone may be obtained in the following manner:

19.1 g of sodium 1,1,1,3,3,3-hexamethyldisilazanate are added to a solution, cooled to −50° C., of 10 g of (4S,5S)-4-methyl-5-phenyl-3-[(2-methoxyphenyl)acetyl]-2-oxazolidinone in 150 cm³ of tetrahydrofuran and the mixture is stirred for 45 minutes at this temperature and then 7.72 cm³ of methyl iodide are added. The reaction mixture is then stirred for 15 hours at room temperature and then diluted with ethyl acetate, washed with 50 cm³ of water and then with 50 cm³ of a saturated aqueous solution of sodium chloride, dried over magnesium sulphate and concentrated to dryness under reduced pressure (2.7 kPa). The residue obtained is crystallized from isopropyl oxide, drained and dried. 4.2 g of (4S,5S)-4-methyl-5-phenyl-3-[(S)- 2-(2-methoxyphenyl)-propionyl]-2-oxazolidinone are obtained in the form of a white solid.

(4S,5S)-4-Methyl-5-phenyl-3-(2-methoxy-phenylacetyl)-2-oxazolidinone may be obtained in the following manner:

9.38 g of 2-methoxyphenylacetic acid are added to a suspension of 1.89 g of sodium hydride (80% dispersion in vaseline) in 200 cm³ of dry tetrahydrofuran, at room temperature. This suspension is cooled to −30° C. 7.77 cm³ of pivaloyl chloride are added and then a solution, cooled to −78° C., which is obtained by adding 35.27 cm³ of a 1.6M solution of butyllithium in hexane to a solution, cooled to −78° C., of 10 g of (4S,5S)-4-methyl-5-phenyl-2-oxazolidinone in 200 cm³ of dry tetrahydrofuran is finally added. The reaction mixture is stirred for 45 minutes at −30° C. and after re-equilibrating to room temperature, 200 cm³ of a saturated aqueous solution of ammonium chloride are added followed by 500 cm³ of ethyl acetate; after decantation, the organic phase is washed twice with 100 cm³ of water and then twice with 100 cm³ of a saturated aqueous solution of sodium chloride; dried over magnesium sulphate and concentrated to dryness under reduced pressure (2.7 kPa). The residue is chromatographed on a silica gel column (particle size 0.04–0.06 mm, diameter 4.8 cm, height 36 cm), eluting under a nitrogen pressure of 0.6 bar with a cyclohexane and ethyl acetate mixture (85/15 followed by 80/20 by volume) and collecting fractions of 50 cm³. Fractions 14 to 31 are pooled and concentrated to dryness under reduced pressure (2.7 kPa). 13.6 g of (4S,5S)-4-methyl-5-phenyl-3-(2-methoxyphenylacetyl)-2-oxazolidinone are obtained in the form of a yellow oil.

Example of use 8

By carrying out the procedure according to that described in the Example of use 9 below, using 0.77 g of 2-dimethylaminophenylacetic acid and 1.50 g of (3aRS,7aRS)-4,4-diphenyl-7,7-difluoroperhydroisoindole hydrochloride, 1.29 g of (3aRS,7aRS)-2-[(2-dimethylaminophenyl)acetyl]-4,4-diphenyl-7,7-difluoroperhydroisoindole are obtained in the form of a white solid; melting point 189° C.

Example of use 9

0.49 g of N,N'-carbonyldiimidazole is added to a solution of 0.52 g of 2-dimethylaminophenylacetic acid in 20 cm³ of dry dichloromethane. The mixture is stirred for 30 minutes at +5° C. and then a solution of 0.93 g of (3aR,4S,7aR)-7,7-diphenyl-4-perhydroisoindolol hydrochloride and 0.84 cm³ of triethylamine in 10 cm³ of dichloromethane is added. The reaction mixture is stirred for 2 hours at +5° C. and then washed with 10 cm³ of water, dried over magnesium sulphate, filtered and concentrated to dryness under reduced pressure (2.7 kPa). The residue obtained is chromatographed on a silica gel column (0.04 mm –0.06 mm, diameter 2 cm, height 35 cm), eluting with ethyl acetate and collecting fractions of 30 cm³. Fractions 8 to 27 are pooled and concentrated to dryness under reduced pressure (2.7 kPa). The residue is crystallized from a mixture of 4 cm³ of acetonitrile and 20 cm³ of ethyl ether. The crystals are drained and dried under reduced pressure (2.7 kPa). 0.70 g of (3aR,4S,7aR)-2-[(2-dimethylaminophenyl)acetyl]-7,7-diphenyl- 4-perhydroisoindolol is obtained in the form of a white solid; melting point 160° C., $[\alpha]^{20}_D$=–162° (c =0.5, methanol).

Example of use 10

By carrying out the procedure according to that described in the Example of use 9, using 0.26 g of 2-dimethylaminophenylacetic acid and 0.50 g of (3aR,4R,7aR)-7,7-diphenyl-4-perhydroisoindolol hydrochloride, 0.21 g of (3aR,4R,7aR)-2-[(2dimethylaminophenyl)acetyl]-7,7-diphenyl-4-perhydroisoindolol is obtained in the form of a white solid; melting point 204° C., $[\alpha]^{20}_D$=–212° (c =0.5, methanol).

Example of use 11

0.42 cm³ of triethylamine and 0.49 g of carbonyldiimidazole are added to a solution, cooled to +4° C., of 0.86 g of (2-pyrrolidinophenyl)acetic acid hydrobromide in 20 cm³ of dry dichloromethane. The mixture is stirred for one hour at +4° C. and then a solution of 1 g of (3aR,4S,7aR)-7,7-diphenyl-4-perhydroisoindolol hydrochloride and 0.42 cm³ of triethylamine in 10 cm³ of dry dichloromethane is added. The reaction mixture is stirred at room temperature for 24 hours and then then washed twice with 10 cm³ of water and then with an aqueous solution of sodium hydrogen carbonate, dried over magnesium sulphate, filtered and concentrated to dryness under reduced pressure (2.7 kPa). The product, which is obtained in the form of a base, is converted to the hydrochloride by dissolving in a minimum amount of acetone and treating with a solution of hydrochloric acid in ethyl ether and adding ethyl ether. The solid obtained is triturated in ethyl ether and then dried. 0.2 g of (3aR,4S,7aR)-7,7-diphenyl- 2-[(2-pyrrolidinophenyl)acetyl]–4-perhydroisoindolol hydrochloride is obtained in the form of a beige solid.

Infrared spectrum (KBr, characteristic bands, cm–1): 3085, 3050, 3025, 2945, 2880, 2750, 2250, 1640, 1600, 1495, 1445, 1060, 755, 730, 700.

Proton NMR spectrum (DMSO-$d_6$): 0.92 and 1.72 (2 mt, 2×1H, $CH_2$—in 5); 2.17 (mt, 4H, 2 $CH_2$ in 3 and 4 of pyrrolidino); 7 to 7.8 (mt, 14H, aromatics).

Example of use 12

By carrying out the procedure as described in Example 9 above, using 1.82 g of (2-methoxyphenyl)acetic acid and 3.29 g of (3aR,4S,7aR)-7,7-diphenyl- 4-perhydroisoindolol hydrochloride, 3.9 g of (3aR,4S,7aR)-2-[(2-methoxyphenyl)acetyl]-7,7-diphenyl-4-perhydroisoindolol are obtained in the form of a white solid; melting point 246° C. $[\alpha]^{20}_D$=–174° (c =0.37); methanol)

Example of use 13

0.37 g of carbonyldiimidazole is added to a solution, cooled to +4° C., of 0.41 g of (S)-2-(2-methoxyphenyl)propionic acid in 15 cm³ of dry dichloromethane. The mixture is stirred for one hour at +4° C. and then a solution of 0.75 g of (3aR,4S,7aR)-7,7-diphenyl- 4-perhydroisoindolol hydrochloride is added. The reaction mixture is stirred at room temperature for 20 hours and then then washed twice with 10 cm³ of water, dried over magnesium sulphate, filtered and concentrated to dryness under reduced pressure (2.7 kPa). The residue is chromatographed on a silica gel column (particle size 0.04–0.06 mm, diameter 3.6 cm, height 37 cm), eluting under a nitrogen pressure of 0.5 bar with an ethyl acetate and cyclohexane mixture (50/50 by volume) and collecting fractions of 50 cm³. Fractions 21 to 41 are pooled and concentrated to dryness under reduced pressure (2.7 kPa). The residue is triturated in isopropyl oxide and then dried. 0.3 g of (3aR,4S,7aR)-7,7-diphenyl-2-[(S)-2-(2-methoxyphenyl)propionyl]–4-perhydroisoindolol is obtained in the form of a white meringue.

Infrared spectrum (KBr, characteristic bands, cm⁻¹): 3090, 3060, 3030, 2940, 2875, 2840, 1630, 1600, 1495, 1445, 1245, 1060, 755, 730, 700.

Proton NMR spectrum (DMSO-$d_6$) (at room temperature, a mixture of the two rotamers is observed): 0.9–1.8 (mt, 2H, $CH_2$ in 5); 1.14 and 1.23 (2d, J=7, 3H, $CH_3$); 3.55 and 3.65 (2 s, 3H, $OCH_3$); 3.85 and 4.23 (2 mt, 1H, —$COCHCH_3$—); 6.8 to 7.5 (mt, 14H, aromatics).

Example of use 14

0,766 g of 1-(3-dimethylaminopropyl)-3-ethylcarbodiimide is added to a solution, cooled to +10° C., of 1 g of (3aR,4S,7aR)-7,7-diphenyl-4-perhydroisoindolol, 0.97 g of 2-(3-dimethylaminopropoxy)phenylacetic acid, 0.05 g of 1-hydroxybenzotriazole in 50 cm³ of dichloromethane. The reaction mixture is stirred for 90 minutes 20° C. and then washed twice with 50 cm³ of water and with 50 cm³ of a saturated solution of sodium chloride. The organic phase is dried over magnesium sulphate and concentrated to dryness under reduced pressure (2.7 kPa). The residue is chromatographed on a silica gel column (particle size 0.2–0.063 mm, diameter 2.9 cm, height 23 cm), eluting under a nitrogen pressure of 0.7 bar with 1,2-dichloroethane and methanol mixtures (1 liter at 90/10 by volume, 1.5 liter at 70/30 by volume) and collecting fractions of 25 cm³. Fractions 10 to 84 are pooled and concentrated to dryness under reduced pressure (2.7 kPa) to give 1.1 g of (3aR,7S,7aR)-2-{[2-(3-dimethylaminopropoxy)phenyl]acetyl}7,7-diphenyl-4-perhydroisoindolol in the form of a cream-colored meringue.

Infrared spectrum (KBr, characteristic bands, cm⁻¹): 3080, 3050, 3020, 2940, 2870, 2815, 2765, 1635, 1600, 1490, 1455, 1445, 1245, 1065, 750, 730, 700.

Proton NMR spectrum (DMSO-$d_6$) at 433° K: 1.06 and 1.76 (2 mt, 2×1H, $CH_2$ in 5); 2.27 (s, 6H, $N(CH_3)_2$); 3.9 (d, J=11, 1H, 1H of $CH_2$ in 3); 6.8 to 7.5 (mt, 14H, aromatics)

A solution of 100 g of 2-hydroxyphenylacetic acid, 75 cm³ of benzyl alcohol and 0.5 g of paratoluenesulphonic acid in 1400 cm³ of toluene is refluxed for 2 hours while removing the water formed. After cooling, treating with 3 g of animal black and filtering, the reaction mixture is concentrated to 150 cm³ and supplemented with 300 cm³ of isopropyl oxide. The crystals obtained by cooling to 0° C. are drained, washed and dried to give 82.5 g of benzyl 2-hydroxyphenylacetate. 174 g of potassium carbonate are added to a solution of 153 g of this ester in a mixture of 500 cm³ of 1,3-dibromopropane and 2500 cm³ of acetonitrile and the mixture is refluxed for 17 hours. The reaction mixture is cooled, filtered and concentrated to dryness under reduced pressure (2.7 kPa). The residue is taken up in 500 cm³ of ethyl acetate and the organic phase is washed twice with 400 cm³ of water and twice with 250 cm³ of a saturated solution of sodium chloride and then dried and concentrated to dryness under reduced pressure (2.7 kPa). The residue is chromatographed on a silica gel column (particle size 0.2–0.063 mm, diameter 9 cm, height 55 cm), eluting with a cyclohexane and ethyl acetate mixture (95/5 by volume) and collecting fractions of 500 cm³. Fractions 12 to 18 are pooled and concentrated to dryness under reduced pressure (2.7 kPa) to give 90 g of benzyl 2-(3-bromopropoxy)phenylacetate in the form of a yellow oil. A solution of 40 g of this product in 500 cm³ of acetonitrile is heated in an autoclave with 27 g of sodium iodide and 90 g of dimethylamine for 16 hours at 80° C. The reaction mixture is cooled, filtered and concentrated to dryness under reduced pressure (2.7 kPa). The residue is purified by acid-base treatment to give 29.3 g of benzyl 2-(3-dimethylaminopropoxy)phenylacetate in the form of a yellow oil. Hydrogenation of this ester at atmospheric pressure at 40° C. in ethyl acetate in the presence of palladium hydroxide, followed by crystallization from ethyl acetate, lead to 17.5 g of 2-(3-dimethylaminopropoxy)phenylacetic acid in the form of white crystals; melting point 98° C.

Example of use 15

A solution of 0.6 g of (3aR,7R,7aR)-4,4-diphenyl-7-fluoroperhydroisoindole hydrochloride and 0.51 cm³ of triethylamine in 10 cm³ of dry dichloromethane is added to a solution of 0.41 g of ethyl (2-methoxyphenyl)acetimidate tetrafluoroborate in 10 cm³ of dry dichloromethane. The reaction mixture is refluxed for 3 hours. It is then treated, after re-equilibrating to room temperature, with 5 cm³ of a 10% aqueous solution of potassium carbonate; the organic phase is washed with 10 cm³ of distilled water, dried over magnesium sulphate and concentrated to dryness under reduced pressure (2.7 kPa). The residue is chromatographed on a silica gel column (particle size 0.04–0.06 mm, diameter 2 cm, height 20 cm), eluting under a nitrogen pressure of 0.6 bar with an ethyl acetate, acetic acid and water mixture (15/1/1 by volume) and collecting fractions of 25 cm³.

Fractions 24 to 38 are pooled and concentrated to dryness under reduced pressure (2.7 kPa). The residue is taken up in 40 cm³ of dichloromethane, washed with 10 cm³ of a saturated aqueous solution of potassium carbonate and then with 10 cm³ of a saturated aqueous solution of sodium chloride. The organic phase is dried over magnesium sulphate and concentrated to dryness under reduced pressure (2.7 kPa). The residue is crystallized from isopropyl oxide. The crystals are drained and dried. 0.18 g of (3aR,7R,7aR)-4,4-diphenyl-7-fluoro-2-[1-imino- 2-(2-methoxyphenyl)ethyl]perhydroisoindole is obtained in the form of white crystals; melting point 184° C., with decomposition.

Example of use 16

A solution of 1.56 g of ethyl (2-methoxyphenyl)acetimidate tetrafluoroborate and 0.96 cm³ of triethylamine in 20 cm³ of dry dichloromethane is added to a solution of 2 g of (3aR,4S,7aR)-7,7-diphenyl-4-perhydroisoindolol in 30 cm³ of dry dichloromethane, and then the reaction mixture is refluxed for 2 hours. 10 cm³ of a 10% aqueous solution of potassium carbonate are then added, decanted and then the organic phase is washed with 20 cm³ of water, dried over magnesium sulphate, filtered and concentrated to dryness under reduced pressure (2.7 kPa). The residue is chromatographed on an alumina column (diameter 3.6 cm, height 31 cm), eluting under a nitrogen pressure of 0.1 bar with a dichloromethane and methanol mixture (95/5 by volume) and collecting fractions of 50 cm³. Fractions 5 to 30 are pooled and concentrated to dryness under reduced pressure (2.7 kPa). The solid obtained is washed with isopropyl oxide, drained and dried. 1.4 g of (3aR,4S,7aR)-7,7-diphenyl- 2-[1-imino-2-(2-methoxyphenyl)ethyl]-4-perhydroisoindolol are obtained in the form of white crystals; melting point 105° C., with decomposition.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

We claim:

1. Perhydroisoindole derivative of the formula:

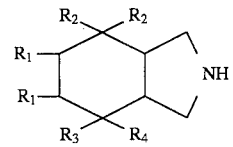

in which the radicals $R_1$ are identical and represent hydrogen atoms or together form a bond, the symbols $R_2$ are identical and represent phenyl radicals which are optionally substituted by a halogen atom or by a methyl radical in position 2 or 3, the symbol $R_3$ represents a halogen atom or a hydroxyl radical and the symbol $R_4$ represents a hydrogen atom or, together with $R_3$, each represent a halogen atom, in its stereoisomeric forms or mixtures thereof, as well as its salts.

2. A perhydroisoindole derivative according to claim 1, wherein:

the radicals $R_1$ are hydrogen atoms, the symbols $R_2$ are identical and represent phenyl radicals, the symbol $R_3$ represents a fluorine or chlorine atom or a hydroxyl radical, and the symbol $R_4$ represents a hydrogen atom or, together with $R_3$, each represent a fluorine atom, in its stereoisomeric forms or mixtures thereof, as well as its salts.

3. A perhydroisoindole derivative according to claim 1, which is 7,7-diphenyl-4-perhydroisoindolol, in its stereoisomeric forms or mixtures thereof, as well as its salts.

4. A perhydroisoindole derivative according to claim 1, which is 4,4-diphenyl-7-fluoroperhydroisoindole, in its stereoisomeric forms or mixtures thereof, as well as its salts.

5. A perhydroisoindole derivative according to claim 1, which is 4,4-diphenyl-7,7-difluoroperhydroisoindole, in its stereoisomeric forms or mixtures thereof, as well as its salts.

6. A perhydroisoindole derivative according to claim 1, which is 7-chloro-4,4-diphenylperhydroisoindole, in its stereoisomeric forms or mixtures thereof, as well as its salts.

\* \* \* \* \*